(12) United States Patent
Luttrull et al.

(10) Patent No.: US 10,194,798 B1
(45) Date of Patent: Feb. 5, 2019

(54) MEASURING RPE AND CHOROID MELANIN LEVELS WITH REFLECTOMETER

(71) Applicant: Ojai Retinal Technology, LLC, Ojai, CA (US)

(72) Inventors: Jeffrey K. Luttrull, Ojai, CA (US); David B. Chang, Tustin, CA (US)

(73) Assignee: Ojai Retinal Technology, LLC, Ojai, CA (US)

( * ) Notice: Subject to any disclaimer, the term of this patent is extended or adjusted under 35 U.S.C. 154(b) by 0 days.

(21) Appl. No.: 15/818,216

(22) Filed: Nov. 20, 2017

(51) Int. Cl.
| | |
|---|---|
| *A61B 3/10* | (2006.01) |
| *A61B 3/12* | (2006.01) |
| *A61B 3/00* | (2006.01) |
| *A61B 5/1455* | (2006.01) |
| *A61B 5/145* | (2006.01) |

(52) U.S. Cl.
CPC .............. *A61B 3/12* (2013.01); *A61B 3/0008* (2013.01); *A61B 5/1455* (2013.01); *A61B 5/14546* (2013.01)

(58) Field of Classification Search
CPC ... A61B 3/0008; A61B 3/0016; A61B 3/0025; A61B 3/0058; A61B 3/0075; A61B 3/10; A61B 3/12; A61B 3/102; A61B 3/152; A61B 3/156; A61B 3/1176; A61B 3/1208; A61B 3/1225; A61B 3/1241; A61B 5/0059; A61B 5/0066; A61B 5/0068; A61B 5/0095; A61B 5/0275; A61B 5/14546; A61B 5/1455; A61B 5/14552; A61B 5/14555; A61B 5/411; A61B 5/415; A61B 5/418; A61B 5/4866; A61B 5/7257; A61N 5/06; A61N 5/067; A61N 5/0613; A61F 9/008; A61F 9/00821; A61F 9/00823
USPC ....... 351/200, 205, 206, 210, 211, 214, 221, 351/246; 359/619; 362/553, 259, 276; 382/106, 128; 600/424, 407, 473–478
See application file for complete search history.

(56) References Cited

U.S. PATENT DOCUMENTS

| | | |
|---|---|---|
| 6,276,798 B1 | 8/2001 | Gil et al. |
| 6,540,391 B2 | 4/2003 | Lanzetta et al. |
| 7,039,452 B2 | 5/2006 | McClane et al. |
| 7,118,217 B2 | 10/2006 | Kardon et al. |
| 7,467,870 B2 | 12/2008 | van de Kraats et al. |

(Continued)

FOREIGN PATENT DOCUMENTS

WO 2016/075868 A1 5/2016

OTHER PUBLICATIONS

International Search Report for the International application No. PCT/US2017/062834, dated Feb. 12, 2018.

(Continued)

*Primary Examiner* — Mustak Choudhury
(74) *Attorney, Agent, or Firm* — Kelly & Kelley, LLP

(57) ABSTRACT

A process for determining levels or concentrations of melanin within an eye includes generating first and second light beams of a different wavelength. The first and second light beams are applied into the eye, such as a retinal pigment epithelium and choroid of the eye. The amount of light reflected from the eye from the first light beam and the second light beam is measured, such as using a reflectometer. A level or concentration of the melanin within the eye is calculated using the measured amount of light reflected from the eye from the first and second light beams.

18 Claims, 10 Drawing Sheets

(56) References Cited

U.S. PATENT DOCUMENTS

| | | | |
|---|---|---|---|
| 8,308,299 | B2 | 11/2012 | Ramella-Roman et al. |
| 8,326,405 | B2 | 12/2012 | Gellermann et al. |
| 8,485,664 | B2 | 7/2013 | Rowe |
| 8,807,751 | B2 | 8/2014 | Kahn et al. |
| 9,010,935 | B2 | 4/2015 | Cui et al. |
| 9,173,562 | B2 | 11/2015 | Sardar et al. |
| 9,332,905 | B1 | 5/2016 | Sims |
| 2010/0085537 | A1* | 4/2010 | Ramella-Roman .......................... A61B 5/14555 351/205 |
| 2011/0261321 | A1 | 10/2011 | Ramella-Ramon et al. |
| 2012/0092619 | A1 | 4/2012 | Rowe |
| 2013/0028484 | A1 | 1/2013 | Wada et al. |
| 2013/0128227 | A1* | 5/2013 | Cui .......................... A61B 3/12 351/211 |

OTHER PUBLICATIONS

R.R. Anderson and J.A. Parrish (1981) The optics of human skin. J. Invest. Dermatol 77, 13-19.
S. Asano & G. Yamamoto (1975), Light scattering by a spheroidal particle. AppliedOptics 14: 29-50.
R. Bingruber (1984) Choroidal circulation and heat convection at the fundus of the eye: implications for laser coagulation and the stabilization of retinal temperature. Laser Applications in Medicine and Biology, Springer, 277-361.
R.A. Bone, B. Brener, J.C. Gibert (2007) Macular pigment, photopigments, and melanin: distribution in young subjects determined by fourth-wavelength reflectometry. Vis. Res. 47, 3259-3268.
T. Burgoyne, M.N. O'Connor, M.C. Seabra,D.F. Cutler, C.E. Futter (2015) Regulation of melanosome number, shape, and movement in the zebrafish retinal pigment epithelium by OA1 and PMEL. J.Cell Sci.128, 1400-1407.
Chemspider: Melanin (2015) Structure, properties, spectra, suppliers and links for: Melanin, 8049-97-6, www.chemspider.com/Chemical-Structure.4884931.html.
T.C. Chen, C. Chuang, J. Cao, V. Ball, D. Ruch, M.J. Buehler (2014) Excitonic effects from geometric order and disorder explain broadband optical absorption in eumelanin. Nat. Commun. 5.3859 doi: 10.1038/ncomms4859.
A.J. Cox, A.J. DeWeerd, & J. Linden(2002) An experiment to measure Mie and Rayleigh scattering cross sections. Am. J. Phys. 70, 620-625.
A.E. Elsner, S.A. Burns, J.J. Weiter, F.C. Delori (1996) Infrared imaging of sub-retinal structures in the human ocular fundus. Vision Res. 36, 191-205.
V.P. Gabel, R. Birngruber, F. Hillenkamp(1978) Visible and near infrared light absorption in pigment epithelium and choroid in Kyoto, Sh8mizu and K.Osterhuis (Eds.) XXIII Concililium Ophth. (Excerpta Medica)invest. Ophth. 1, 340 Amsterdam: Elsevier.
W.J. Geeraets et al (1962) The relative absorption of thermal energy in retina and choroid.
R.D. Glickman, J.M. Gallas, S.L. Jacques, B.A. Rockwell, D.K. Sardar(2001)Physical and photochemical properties of ocular melanin. Proc. of SPEI 4241,112-123.
M. Hammer, D. Schweitzer, E Thamm, A. Kolb, J. Strobel (2001) Scattering properties of the retina and the choroids determined from OCT-A-scans. Intl. Ophthalmol. 23, 291-295.
S. Jacques (1998) Melanosome absorption coefficient. Oregon Medical Laser Center, http://omic.org.
M. Jastrzebska, A. Kocot, J.K. Vij, J. Zalewska-Rejdak, T. Witecki (2002) Dielectric studies on charge hopping in melanin polymer. J. Molec. Struct. 606, 205-210.
I.T. Kim & J.B. Choi(1998) Melanosomes of retinal pigment epithelium—distribution, shape, and acid phosphatase activity. Korean J. Ophthalmol. 12, 85-91.
P. Kubelka & F. Munk (1931) Ein beitrag zur optick der farbanstriche. Z. Tech. Phys. (Leipzig) 12, 593-601.
I.A. Menon, S. Persad, H.F. Haberman, C.J. Kunan, P.K. Basu (1982) A quantitative study of the melanins from blue and brown human eyes. Exp. Eye Res. 34, 531-537.
P. Meredith & T. Sarna (2006) The physical and chemical properties of melanin. Pigment Cell Res. 19, 572-594.
A.B. Mostert, B.J. Powell, F.L. Pratt, G.R. Hanson, T. Sarna, I.R. Gentle, P. Meredith (2012) Role of semiconductivity and ion transport in the electrical conduction of melanin. PNAS 109, 8943-8947.
S.J. Preece & E. Claridge (2002) Monte Carlo modelling of the spectral reflectance of the human eye. Phys. Med. Biol. 47, 2863-2877.
J. Riesz, J. Gillmore, P. Meredith (2006) Quantitative scattering of melanin solutions. Biophys. J. 90, 4'37/4144.
J. Riesz (2007) The spectroscopic properties of melanin. PhD thesis, University of Queensland.
L.I. Schiff (1955) Quantum Mechanics. New York: McGraw-Hill, 169.
J. van de Kraats ,T.T.J.M. Berendschot, D. van Norren (1996) The pathways of light measured in fundus reflectometry. Vision Res. 36, 2229-2247.
V. Wang and HI. Wu (2007) Biomedical Optics: Principles and Imaging. Wiley. ISBN 978-0-471-74304-0.
J.J. Weiter, F.C. Delori, G.L. Wing, K.A. Fitch (1986) Retinal pigment epithelial lipofuscin and melanin and choroidal melanin in human eyes. Inv. Ophth. Vis. Sci. 27, 145-152.
A.M. Zysk, F.T. Nguyen, A.L. Oldenburg, D.L Marks, S.A. Boopart (2007) Optical coherence tomography: review of clinical development from bench to bedside. J. Biomed. Optics 12, May 14, 2003.

* cited by examiner

MEASURING RPE AND CHOROID MELANIN LEVELS WITH REFLECTOMETER

FIELD OF THE INVENTION

The present invention generally relates to a process for determining melanin levels within an eye. More particularly, the present invention is directed to a process for measuring both retinal pigment epithelium (RPE) and choroid melanin levels using a simple reflectometry process.

BACKGROUND OF THE INVENTION

The importance of macular pigment to the health of the eye has prompted development and interest in methods for measuring its density or concentration in the retina. Prior systems and methods, however, have either been based upon equipment which is not commonly available, is time consuming, or complicated and expensive.

With reference now to FIG. 1, a diagrammatic view of an eye, generally referred to by the reference number 10, is shown. The eye 10 includes a cornea 12 which is a transparent front part of the eye that covers the iris and pupil 14 which is the variable-size black circular or slit-shaped opening in the center of the iris that regulates the amount of light that enters the eye. The lens 16 is a transparent biconvex structure in the eye that, along with the cornea 12, helps to refract light to be focused on the retina 18. The retina is a thin layer of neural cells that line the back of the eyeball which captures light and transforms it into electrical signals for the brain. It has many blood vessels 20 to nourish it. The fovea and macular region, referred to by the reference number 22, is a portion of the eye used for color vision and fine detail vision. The retinal pigmented epithelium (RPE) 24 is the pigmented cell layer just outside the neurosensory retina 18 that nourishes the retinal visual cells. It is firmly attached to an underlying choroid 26 which is a vascular layer of the eye 10 lined between the retina 18 and the sclera. The choroid 26 provides oxygen and nourishment to the outer layers of the retina 18.

Many diseases of the eye are related to the retina and there have been developed methodologies including photocoagulation and photostimulation of the retina to treat such diseases and conditions. Photocoagulation and photostimulation rely upon heating of the retinal tissue to create their therapeutic effects. Excessive heating can damage or even destroy retinal tissue, which in some treatment methodologies is intentional but in others is avoided. It has been found that abnormal levels of pigmentation, particularly levels or concentrations of melanin within the RPE can cause unanticipated and excessive heat during such treatments and potentially damage the retinal tissue.

Melanin in the eye has many important functions which are not yet completely understood. Melanin in the eye provides protection to the eye by absorbing harmful ultraviolet radiation. Melanin also promotes visual acuity by scattering stray light away from the rods and cones and absorbing light reflected from the back of the eye. Melanin serves as an antioxidant to aid in the prevention of retinal diseases, such as age-related macular degeneration.

Many of these properties result from the fact that the absorption spectrum of melanin is very broad. In this respect, it is unique among pigments. Many mechanisms have been suggested for this unique behavior. As examples, the broadband absorption has been attributed to chemical heterogeneity, amorphous semiconducting, and scattering. However, it has been shown that scattering losses only account for a few percent of the broadband attenuation. There are also problems with the chemical heterogeneity and amorphous semiconducting hypothesis. Some have proposed polymeric charge hopping. Others have pointed out the importance of hydration and introducing free radicals into melanin. Yet others have suggested that melanin excitons may play a role in its broadband absorption. There does not appear to be universal agreement that any particular explanation can account for all of melanin's electrical and optical properties.

As indicated above, melanin within the eye serves many important functions. The determination of the levels or concentrations of melanin within the eye can be important to ascertain. For example, laser treatments of eye diseases are based on inducing temperature rises in the RPE, which activates the eye's natural repair mechanisms. In the near infrared, this results from the absorption of the infrared radiation by the melanin pigment in the RPE. Considerable melanin also exists in the choroid behind the RPE, but absorption by the choroidal melanin does not play a significant role in raising the temperature of the RPE due to the lack of diffusive heat transfer to the RPE during the relatively short treatment times and due to the convective cooling by the blood vessels in the choroid and the choriocapillaris.

In laser subthreshold damage treatments of eye diseases, the laser treatment is effective as long as the temperature rise does not exceed the order of 10° C. This temperature rise limitation determines the maximum laser energy that can be absorbed by the RPE during the treatment time. A possible concern, however, is that for laser powers that are suitable for most patients, the temperature rise can exceed the threshold for damage if the patient's RPE melanin concentration is abnormally too large.

Accordingly, there is a continuing need for a simple and relatively inexpensive process for determining melanin levels or concentrations within the eye, and particularly within the RPE of the eye. The present invention fulfills these needs, and provides other related advantages.

SUMMARY OF THE INVENTION

The present invention is directed to a process for determining levels of melanin within an eye which is relatively simple and inexpensive. More particularly, the present invention is directed to a two-wavelength reflectometry process for determining the levels or concentrations of melanin in the RPE and choroid of the eye.

In accordance with the present invention, a first light beam having a wavelength between 550 nm and 900 nm is generated. The first light beam may have a wavelength of between 600 nm and 850 nm. The first light beam is applied into the eye, such as being applied to a retinal pigment epithelium (RPE) and a choroid of the eye. The amount of light reflected from the eye from the first light beam is measured. This may be done by using a reflectometer to measure the amount of light reflected from the eye from the first light beam.

A second light beam having a wavelength between 550 nm and 900 nm is generated. The second light beam may have a wavelength between 600 nm and 850 nm. The second light beam is of a different wavelength than the first light beam. The first and second light beams preferably differ in wavelength by at least 25 nm. The second light beam is applied into the eye, such as to the RPE and choroid of the eye. The amount of light reflected from the eye from the second light beam is measured, such as using a reflectometer.

The level of melanin within the eye is calculated using the measured amount of light reflected from the eye from the first and second light beams. More particularly, the calculating step includes the step of distinguishing the amount of light reflected by the first and second light beams from the RPE and the choroid.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

For purposes of illustration, the present invention is directed to a process for determining concentrations of melanin within an eye, and particularly within the retinal pigment epithelium (RPE) and choroid of the eye. Determining the concentrations or levels of melanin within the RPE and choroid of the eye can be important in determining the health of the eye. For example, melanin functions as an antioxidant to aid in the prevention of retinal diseases, such as age-related macular degeneration. Determining the concentrations of melanin within the RPE or choroid of the eye can also be important in determining treatment of eye diseases. For example, if an individual has elevated concentrations or levels of melanin within the RPE this can cause unanticipated elevated heating, and thus tissue destruction, when treating the eye, and particularly the retina, with light sources, such as infrared or near infrared laser light beams, such as those used in photocoagulation and photostimulation.

The melanin layers within the choroid can vary significantly. However, it is the level or concentrations of melanin within the RPE that is often important to determine as this is the layer which can cause excessive heating and damage when the retina is exposed to light sources during photocoagulation or photostimulation treatments. The invention takes into account the light absorbed and scattered by both the RPE and choroid layers in order to get an accurate picture of the amount of melanin in the RPE. The invention, as will be more fully described herein, utilizes two wavelengths within a predetermined range of wavelengths in which melanin both absorbs and reflects these wavelengths. The wavelengths are distinct from one another, preferably towards the lower end and the upper end of the predetermined wavelength range, and the present invention measures the amount or degree of reflections and then determines the levels or concentrations of melanin within the RPE and choroid by taking into account both the absorption and the scattering or reflections of the two wavelengths.

Figure 1:
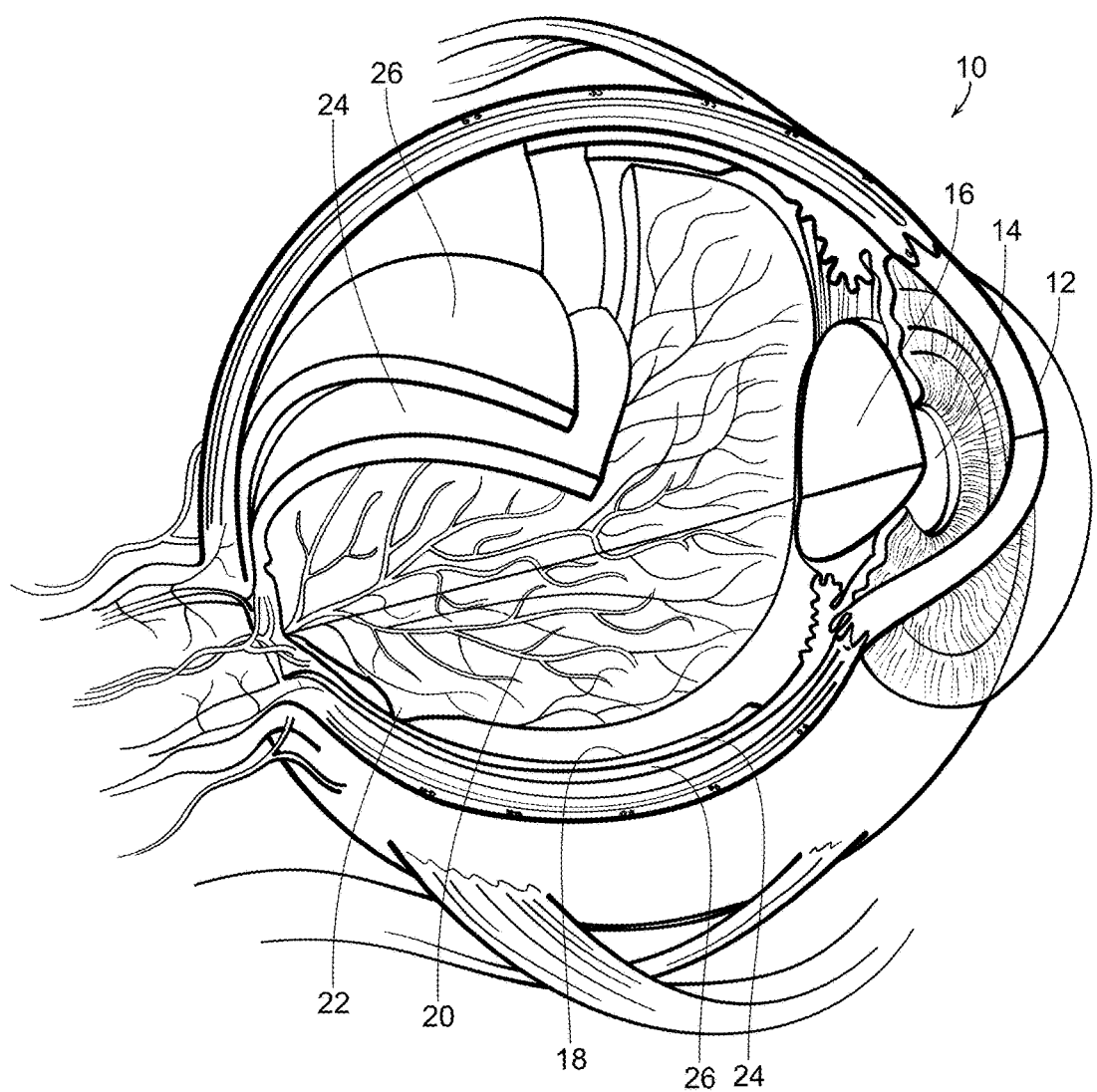
FIG. 1 is a diagrammatic view of an eye.
Figure 2:
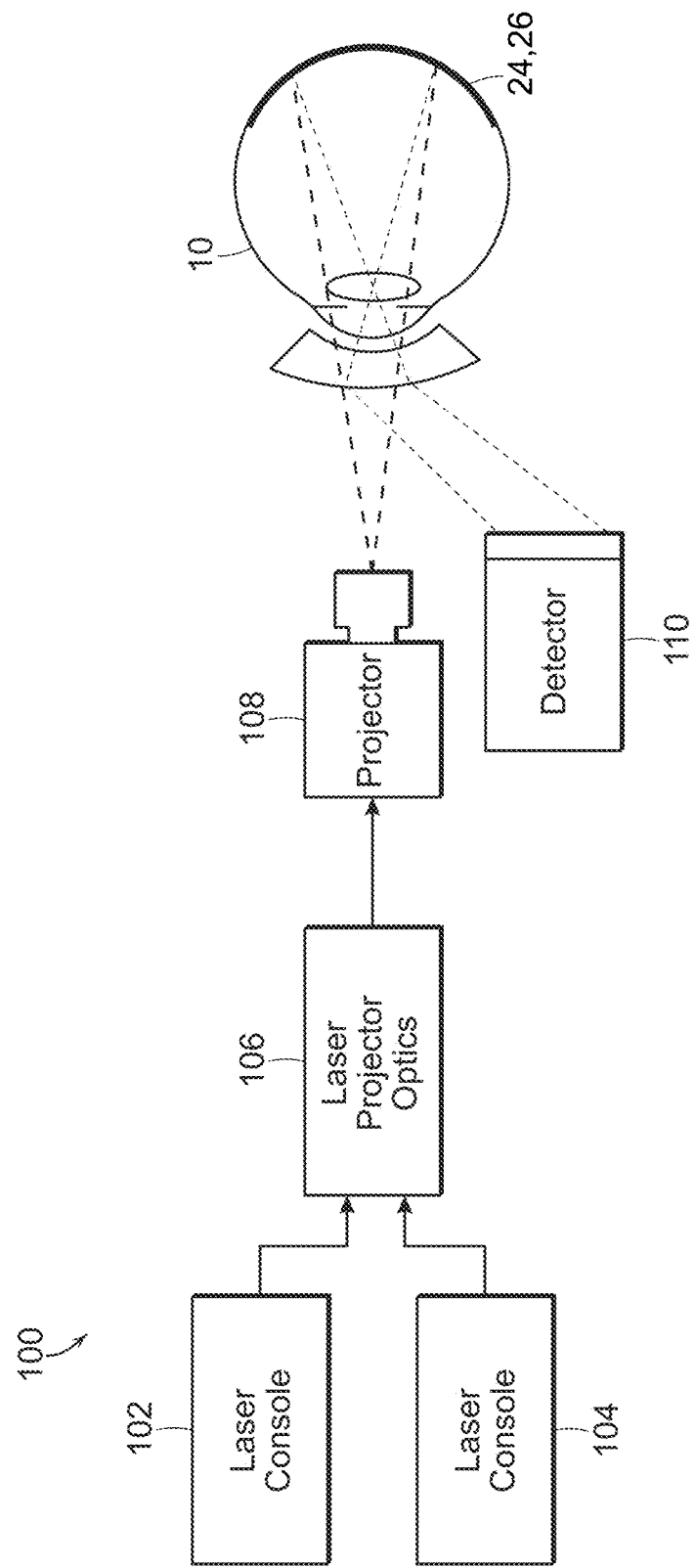
FIG. 2 is a diagrammatic view of a system used in accordance with the present invention for determining concentrations of melanin within portions of an eye.

With reference now to FIG. 2, a system 100 is shown which is used in accordance with the present invention. Laser console 102 generates a first light beam having a wavelength within a predetermined range. The range may be between 550 nm and 900 nm, typically between 600 nm and 850 nm, and more preferably between 625 nm and 800 nm. Wavelengths below the predetermined wavelength range begin to absorb and scatter light from other pigments, and wavelengths above the predetermined range of wavelengths of the present invention are increasingly absorbed by water. However, the predetermined wavelength range of the present invention is ideal for measuring the melanin levels of the RPE and choroid.

The generated light beam is then passed through optics 106, which may be used to focus the light beam, filter the light beam, generate a plurality of light beams from the generated first light beam, or the like. The light beam is then passed through projector 108, which may be a retina camera or the like, for projection into the eye 10, and more particularly so as to apply the first light beam to the RPE 24 and choroid 26 of the eye 10. Reflections from the RPE and choroid are detected by detector 110. The detector 110 in a particularly preferred embodiment is a reflectometer although other detector devices could be utilized such as those using interferometry such as an Optical Coherent Tomography (OCT) device.

With continuing reference to FIG. 2, a second light beam is generated, such as by laser console 104. The second light beam has a wavelength between 550 nm and 900 nm, or 600 nm-850 nm or preferably 625 nm-800 nm, that is a different wavelength than the first light beam. The first and second light beams may differ in wavelength by at least 25 nm, and more preferably are at opposite ends or ranges of the wavelength range so that they can be more easily distinguished from each other when the light reflected by each is detected. The second light beam may pass through optics 106, as described above, and then through projector 108 into the eye 10, and particularly the RPE and choroid 24 and 26 of the eye 10. The light scattered and reflected by the second light beam is detected and measured by detector 110. It will be understood that the first and second light beams generated by consoles 102 and 104 can be applied to the eye 10 sequentially or simultaneously.

The amount of light reflected from the RPE and the choroid by the first and second light beams is measured, and then a concentration of melanin within the RPE and choroid of the eye is determined using the measured amount of light reflected from the RPE and the choroid from the first and second light beams. The invention distinguishes the amount of light reflected by the first and second light beams from the RPE and the choroid and the measurements of the amount of light reflected from the first and second light beams may be applied to calculations and/or graphs or tables to determine the levels or concentrations of melanin within the choroid and more particularly the RPE. The determined level or concentration of melanin within the RPE can then be compared to anticipated or average levels of melanin within the RPE to determine if the melanin levels within the RPE of that eye are elevated or outside of the anticipated range.

The melanin in the eye is primarily eumelanin, and its monomer has the chemical formula $C_{18}H_{10}N_2O_4$, and a molecular weight of 318.283, with a density of 1.7 g/cc and an index of refraction of 1.772. In both the RPE and the choroid, melanin is contained in protein-coded organelles, called melanosomes. Inside the melanosomes, the melanin monomers, which have dimensions of less than ten Angstroms, combine to form aggregates. The aggregates have dimensions of several tens of Angstroms, and are made up of stacked sheets of covalently-bonded monomer, with the sheets having separations of 3.4 Angstroms. The sheets are held together by weaker pi-pi bonding forces.

The melanin in the RPE is derived from the neural ectoderm, whereas the choroidal melanin is derived from the neural crest. The melanosomes in the RPE are different from those in the choroid. In the RPE, the melanosomes are located mainly in the apical region of the RPE cells and are elongated in shape, with the long dimension aligned with the apices in order to make close contact with the rods and cones. Typical widths of all foreign RPE melanosome are 250-500 nm, and typical lengths are 640-800 nm. These give $6.5 \times 10^{-14}$ cubic centimeters for a typical melanosome volume. The melanin is rather densely packed in the RPE melanosomes, the melanin density in a monomer being 1.7 g/cc.

In the choroid, the melanosomes do not need to be elongated and are believed to be globular in shape. The density of melanin in the choroid is less than that in the RPE, with ranges of 3.61-8.05 mmol/L for RPE melanin, and 0.07-9.15 mmol/L for choroidal melanin. However, since the choroid depth is 200 microns compared to 6-10 microns for the REP, there is much more melanin in the choroid than in the RPE.

In the RPE, from the foregoing numbers, the number density of melanin is $3.38 \times 10^{18}$ $CM^{-3}$ with a mass density of $1.8 \times 10^{-3}$ G/cc, and since the melanin is all contained within melanosomes, the corresponding number density of melanosomes in the RPE is $10 \times 10^{10}$ $CM^{-3}$. This gives a linear separation between melanosomes in the RPE of 3.68 microns. In the choroid, on the other hand, the density of melanin is $0.49 \times 10^{-3}$ G/cc, corresponding to a melanosome number density of $5.4 \times 10^9$ $CM^{-3}$. Thus, in the choroid, the linear spacing between the melanosomes is $5.7 \times 10^{-4}$ CM, or 5.7 microns.

Figure 3:
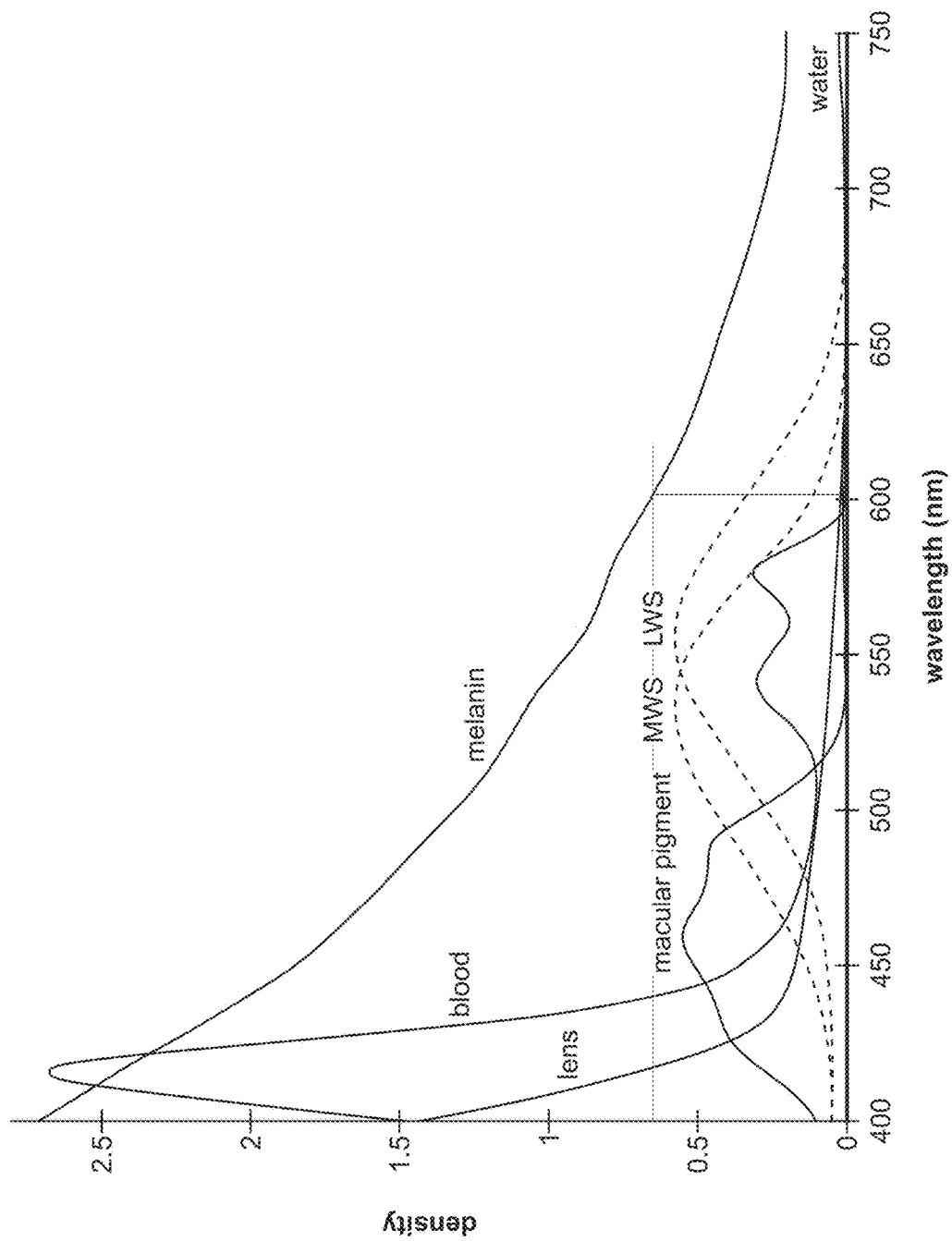
FIG. 3 is a graph illustrating wavelength dependence of the absorption of primary ocular pigments.

With reference now to FIG. 3, the absorption of blood, melanin, macular pigments, the lens, water, long wavelength sensitive visual pigments (LWS) and medium wavelength sensitive visual pigments (MWS) primarily within the visible range of wavelengths is illustrated. The blood layer is taken to be 23 microns thick with an oxygenation of 95%. The melanin density is 1.32 at 500 nm, and the macular density is 0.54 at 460 nm. The lens density is 0.54 at 420 nm and the water density is 0.025 at 740 nm. The visual pigment densities are both 0.57 at their peaks. In the eye, melanin dominates the absorption of laser light in the wavelength range generally between 550 nm and 900 nm, and more particularly between 600 nm and 800 nm as shown in FIG. 3.

Prior modeling of the spectral reflectance of the human eye used values of 3.61-8.05 mmol/L for RPE melanin and values of 0.07-9.15 mmol/L for choroidal melanin. The thickness of the melanin layer in the RPE is less than 10 microns, typically around 6 microns, whereas the choroid thickness is on the order of 200 microns, or approximately 30 times thicker. Thus, much more melanin usually exists in the choroid than in the RPE. Moreover, it has been found that the melanin content in the RPE does not usually vary much from patient to patient, although the choroid melanin can vary widely.

As seen in FIG. 3, the absorption coefficient of melanin decreases considerably as the wavelength increases. Thus, at the lower 600 nm end of the melanin-dominated absorption window, the RPE melanin absorption is much larger than it is at the 800 nm upper end of a particularly preferred range of wavelengths. There is no general agreement as to how the melanin absorption varies with wavelength, however.

Figure 4:
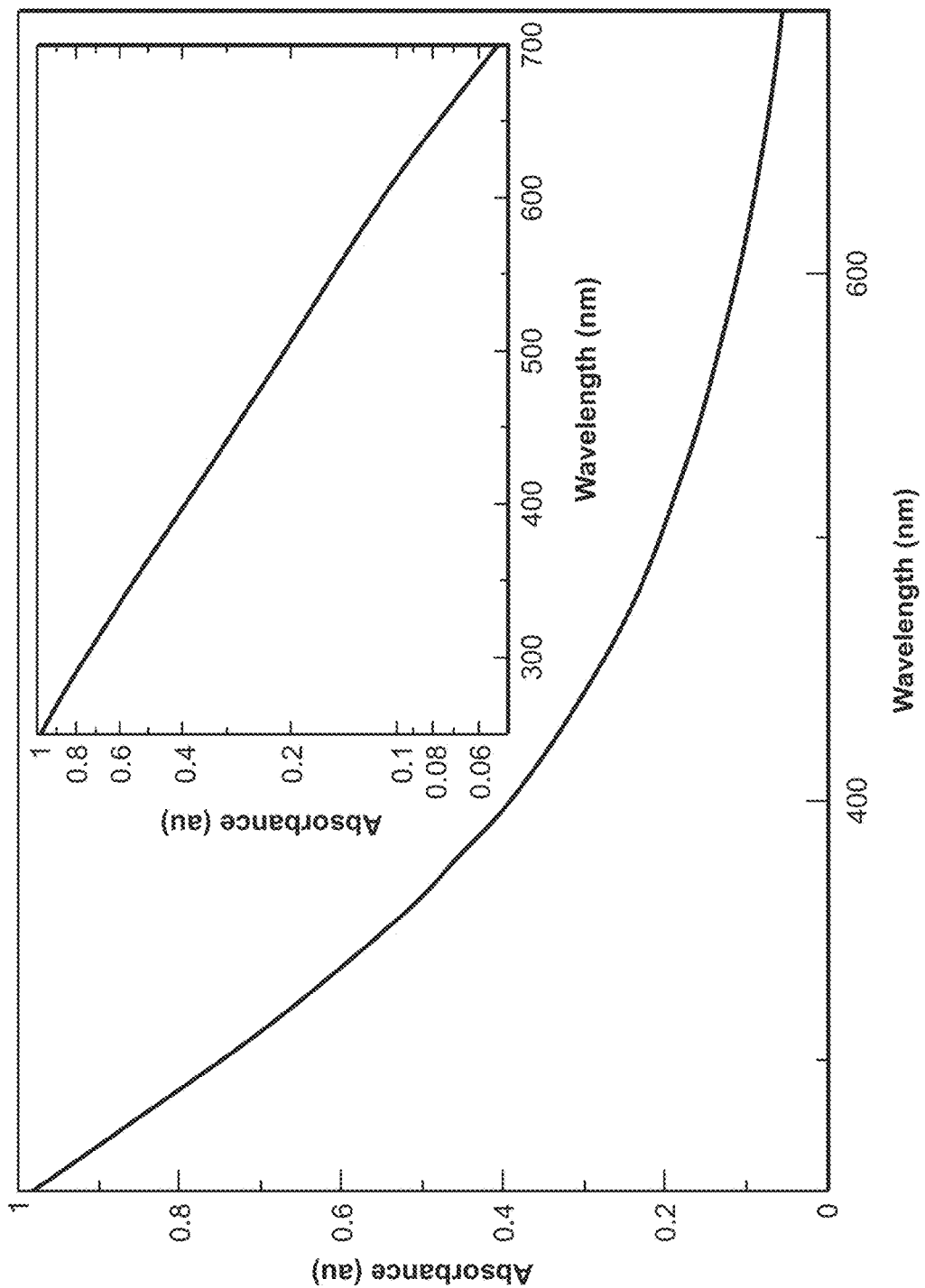
FIG. 4 is a graph illustrating absorbance of eumelanin as a function of wavelength.

FIG. 4 is a graph illustrating the absorbance of eumelanin as a function of wavelength, particularly between 250 nm and 700 nm. Eumelanin is the dominant component of the melanin in the eye. Although there is no general agreement on the variation of the optical density with wavelength, the present invention assumes exponential dependence of exp [−0.062λ (nm)], which is reflected in FIG. 4. If this result is combined with the prior finding of an optical density of 0.22 at 500 nm, this gives for the two-way transmission through the RPE of:

$$\text{Transmission}=\exp[-2\alpha L]=\exp[-22.72\exp[-0.0062\lambda \text{ (nm)}]] \quad [1]$$

On the other hand, if an optical density of 0.29 at 500 nm is used, then the result yields:

$$\text{Transmission}=\exp[-2\alpha L]=\exp[-29.973\exp[-0.0062\lambda \text{ (nm)}]] \quad [2]$$

Figure 5:
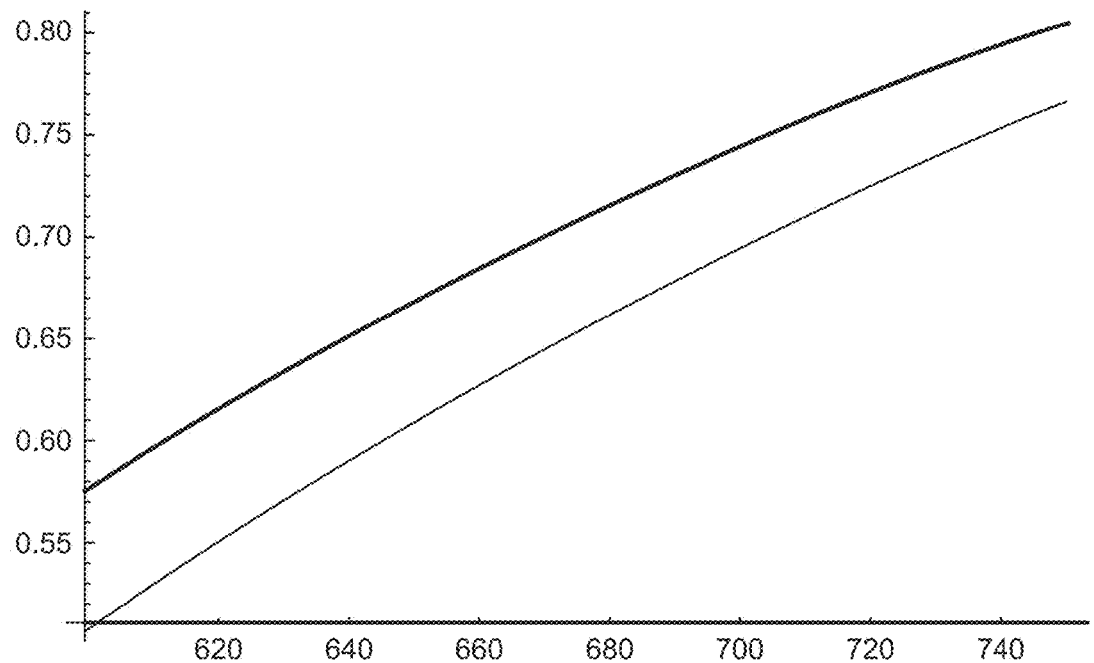
FIG. 5 is a graph depicting two-way transmission through RPE melanin at ordinary concentrations.

Equations [1] and [2] are plotted in FIG. 5, which is a graph depicting the two-way transmission (as determined by the large absorption cross-section) through the RPE melanin at ordinary concentrations. The top curve assumes that the optical density is 0.22 at 500 nm, whereas the lower curve assumes that the optical density at 500 nm is 0.29. It can be seen that towards the 800 nm limit of the melanin-dominated absorption window, the absorption coefficient of the RPE melanin is small, permitting the reflected signal from the choroid to pass through to the detector 110. However, at the 600 nm lower limit, the absorption coefficient of RPE melanin becomes sufficiently large that less of the reflected signal from the choroid can pass through to the detector. At elevated, potentially dangerous, levels of RPE melanin, the reflected signal from the choroid at 600 nm is diminished considerably on passing through the RPE, while at 800 nm is not diminished nearly as much.

Figure 6:
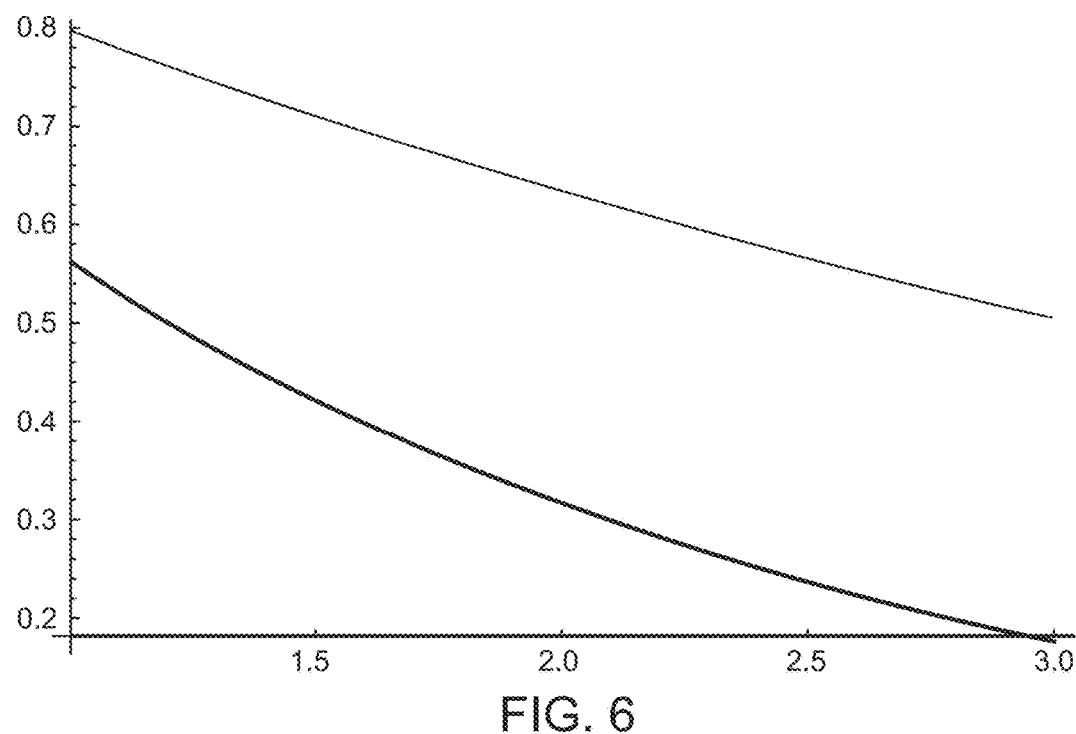
FIG. 6 is a graph illustrating variation of the RPE melanin transmission at different wavelengths.

FIG. 6 is a graph illustrating the variation of the RPE melanin transmission (as determined by the large absorption coefficient) at 750 nm (top curve) and at 600 nm (bottom curve) as the RPE melanin concentration is varied from normal (n=1) to an elevated, danger threshold of three times normal (n=3). In FIG. 6, it is assumed that the optical density of 500 nm is 0.22 for a normal RPE concentration. With continuing reference to FIG. 6, the graph shows the behavior of the RPE melanin transmission at 600 nm and 750 nm as the concentration is varied from normal (n=1) to a dangerous level of three times normal (n=3). The graph of FIG. 6 shows that at 600 nm the transmitted signal is diminished by a factor of close to 4, while at 750 nm it is only diminished by a factor of approximately 1.5. This large difference, however, may be mitigated somewhat by other factors in the expression for reflectivity.

By contrast, the optical path in the melanin in the choroid is larger. It has been estimated that the typical density of melanin in the RPE is 5.82 mmol/L, and since the molecular weight of melanin monomer is 318.283, a weight density of $1.86 \times 10^{-3}$ G/CC is given. This occupies a region of thickness of 6-10 microns. For the choroid, a typical density of 1.59 mmol/L, i.e. $0.51 \times 10^{-3}$ G/CC, but the thickness of the choroid is 200 microns. Thus, if the optical density of the RPE melanin is 0.22 at 500 nm, the choroid melanin has an optical density at 500 nm of 2.00. Thus, one-way transmission from the back to the front of the choroid is only $\exp[-2.303 \times 2.00]=0.01$. Thus, most of the radiation is absorbed. This means that the reflection from the sclera does not contribute appreciably to the reflection signal. However, there is considerable variation in the choroid melanin content in different eyes and patients, so it is important in general to take account of the contribution of a reflection from the sclera.

Melanin is densely packed in the melanosomes. As described above, in the RPE the melanosomes are elongated in shape and make close contact with the rods and cones. In the choroid, on the other hand, the melanosomes are believed to be globular in shape. The melanosomes are regarded as the basic scattering entities. The melanosomes have dimensions comparable to the 600 nm-800 nm wavelengths of interest. A typical RPE melanosome has dimensions of 250-400 nm (average 300 nm) wide by 640 nm-800 nm (average 720 nm) long. It is assumed that a globular choroid melanosome has a comparable volume to an RPE melanosome, so as to have a radius of $2.5 \times 10^{-5}$ CM, i.e. 250 nm.

For dielectric spherical scatterers, when the radiation wavelength is much larger than the size of the scatter, the cross-section for the scattering may be given by the Rayleigh expression:

$$\sigma_{Rayleigh}=(8\pi/3)(ka)^4 a^2\{(K_{rel}-1)/(K_{rel}+2)\}^2 \qquad [3a]$$

Whereas when the wavelength is comparable to the size of the scatterer, the cross section is expressed in terms of the Mie sum over an infinite series of Legendre polynomials. At small wavelengths, the Mie expression for the total scattering cross section reduces to the asymptotic value:

$$\sigma_{sphere}=2\pi a^2 \qquad [3b]$$

In eqs. [3a] and [3b], the wave number k is:

$$k=2\pi n_{med}/\lambda \qquad [3c]$$

and
   a=radius of scattering sphere
   $n_{med}$=index of refraction of the medium in which the sphere is immersed
   λ=vacuum wavelength of the radiation
   $K_{rel}=n_{sphere}/n_{med}$
   $n_{sphere}$=index of refraction of the sphere When ka=O(1), the cross section oscillates a little as it approaches its asymptotic value of $\sigma_{sphere}=2\pi a^2$.

Another important difference in the behavior of the scattering at long and short wavelengths is that at long wavelengths, there are approximately as many scattering events in the forward as in the backward direction. At short wavelengths, however, this changes dramatically when ka>1, the scattering is predominantly in the forward direction. The scattering angles are contained mainly in a cone of angle:

$$\Theta=O(1/ka) \qquad [4]$$

Thus, on applying the Born approximation to a spherical scatterer of radius a, it can be shown that:

$$<\cos \Theta>=g[2ka \sin \theta] \qquad [5a]$$

where $$g(x)=(\sin x - x \cos x)^2/x^6 \qquad [5b]$$

When ka>>1, this reduces to:

$$<\cos \Theta>=1-(5/4)(1/(ka))^2 \qquad [5c]$$

showing that at short wavelengths, the scattering angle is very small.

The cross section a for a sphere to scatter in backward directions when ka>>1 is then:

$$\sigma_{s \, SPHERE}=2\pi a^2[1-<\cos \Theta>]=2\pi a^2(5/4)(1/(ka))^2=(5/8\pi)\lambda^2=0.08\lambda^2 \qquad [5d]$$

in the Born approximation, independent of its radius, and just proportional to the square of the wavelength. Since eq. [5d] is derived using the Born approximation, the 0.08 coefficient may not be correct, but the dependence on $\lambda^2$ is believable since it results from diffraction on a sphere of radius a.

The melanosomes in the RPE are not spherical in shape, but are elongated with their long dimensions oriented parallel to the axes of the rods and cones. The melanosomes are comprised of melanin aggregates made up of stacked sheets of covalently bonded melanin monomers.

Figure 7:
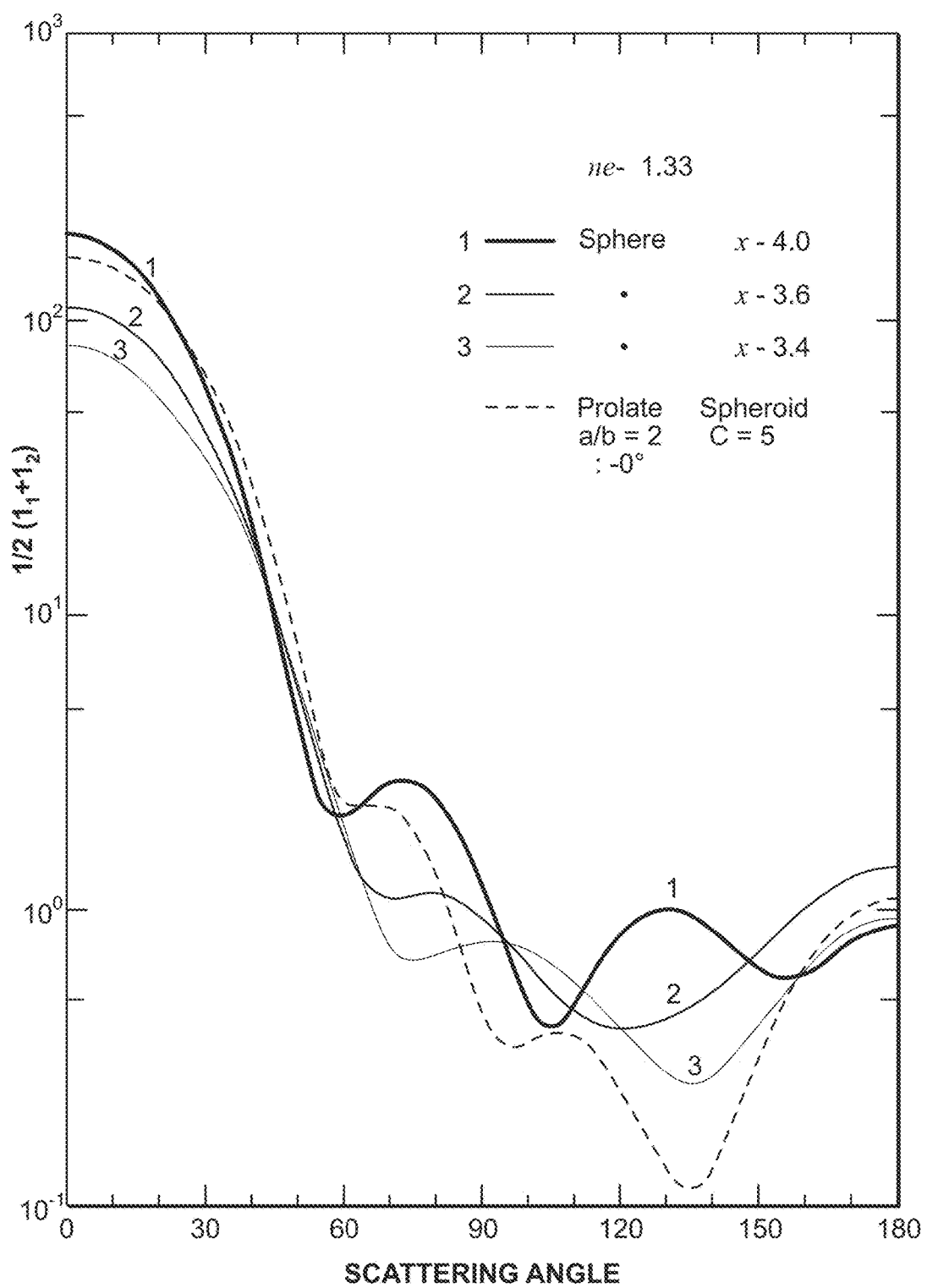
FIG. 7 is a graph illustrating angular distribution of an intensity function that is proportional to the differential cross-section for scattering from a prolate spheroid and spheres.

With reference to FIG. 7, a graph provides the information needed to estimate the scattering cross-section of a prolate spheroid that has the dimensions of an RPE melanosome. FIG. 7 shows angular distribution of an intensity function that is proportional to the differential cross-section for scattering from a prolate spheroid with a/b=2 and kc=5 (dashed line), and from three spheres for comparison (solid lines). The solid line curve labeled "2" is for a sphere of the same volume as a prolate spheroid. The figure shows the resemblance of the scattering behavior to that described by Mie scattering from spheres.

In FIG. 7, the semi major axis of the prolate spheroid is denoted by "a" and corresponds to one-half of the 720 nm (640-800 nm) dimension of the RPE melanosome. The semi minor axis of the prolate spheroid is denoted by "b", and corresponds to one-half of the 300 nm (250-400 nm) dimension of the RPE melanosome. The wave number defined in equation [3c] is "k". The semifocal distance is $c=(a^2-b^2)^{1/2}$. The radiation is assumed to be incident on the prolate spheroid along its major axis. The aspect ratio (a/b=2) of the prolate spheroid in FIG. 7 is comparable to that of an RPE melanosome (a/b=2.4 on average).

The differential cross section for scattering is proportional to the intensity function of the ordinate in the figure. Accordingly, measurement of the areas under the dashed curve and under the solid curve of the sphere of equal volume (labeled "2") in the figure reveals that the cross section for forward scattering (0 to 90 degrees) in the prolate spheroid is 1.45 times that for forward scattering from a sphere of equal volume. Also, the cross section for backwards scattering (90-180 degrees) in the prolate spheroid is 0.6 that for backwards scattering from a sphere of equal volume. That means that a choroidal melanosome is 1.65 times more effective than an RPE melanosome in scattering radiation in the backwards direction. For the sphere, the ratio of the backwards scattering cross section to the total scattering cross section is 0.018, i.e. only 1.8% of the scattered radiation is in the backwards direction. This is consistent with our earlier observation that most of the radiation is scattered in a small cone about the forward direction (eq. [4]).

Taking the total scattering cross section of the sphere to be $2\pi a^2$ (eq. [3b]), the last observation allows us to say that the sphere's cross section for backwards scattering is:

$$\sigma_s(\text{sphere}) = 0.018 \times 2\pi a^2 = 0.018 \times 2\pi \times (2.5 \times 10^{-5})^2 = 0.707 \times 10^{-10} \text{ cm}^2 \quad [6]$$

at a wavelength corresponding to kc=5.

To determine the wavelength for which eq. [6] applies, examine the expression for kc=5:

$$Kc = ka[1-(b/a)^2]^{1/2} = 5 \quad [7a]$$

i.e.

$$(2\pi/\lambda)360[1-0.25]^{1/2} = 5 \quad [7b]$$

This gives $\lambda$=39 nm. Accordingly, since eq. [5d] indicates that the backwards scattering cross section should be proportional to $\lambda^2$, we find for a general wavelength less than $2\pi a$=1571 nm, $$\sigma_{sCH} \approx 0.43 \times 10^{-10} (\lambda_{nm}/392)^2 = 0.05\lambda^2 \text{ cm}^2 \quad [8a]$$

This is a little smaller than the $0.08\lambda^2$ cm$^2$ Born approximation result of eq. [5d]. From the measured 0.6 ratio of the backwards scattering cross sections of prolate spheroids and spheres of the same volume in FIG. 7, and the expected diffraction-related origin of the $\lambda^2$ dependence, we then write for the backwards scattering cross section of an RPE melanosome:

$$\sigma_{sRPE} \approx 0.03\lambda^2 \text{ cm}^2 \quad [8b]$$

When $\lambda$ is expressed in terms of nm, eqs. [8] and [9] become:

$$\sigma_{sCH} \approx 0.03 \times 10^{-14} \lambda_{nm}^2 \text{ cm}^2 \quad [9a]$$

$$\sigma_{sRPE} \approx 0.05 \times 10^{-14} \lambda_{nm}^2 \text{ cm}^2 \quad [9b]$$

Although the absorption is dominated by the melanin in the 600 nm-800 nm range of wavelengths, scattering can also result from the structural matrix in which the melanosomes are embedded. Prior research has determined the scattering properties of the retina and the choroid from OCT scans. For a wavelength of 855 nm:
Retina:
Scattering coefficient $1.64 \times 10^{-4} \lambda_{nm}^2$ $_{tRET}$=120 cm$^{-1}$
Anisotropic factor $g_{RET} = <\cos\theta> = 0.97$
Choroid:
Scattering coefficient $\mu_{scatCH}$=275 cm$^{-1}$
Anisotropic factor $g_{CH}$=0.90

With the large anisotropic factor, the backwards scattering coefficient is obtained from the scattering coefficient by multiplying it by (1–g).

The scattering occurs due to mismatches in refractive index of the different tissue components, ranging from cell membranes to whole cells. Cell nuclei and mitochondria are the most important scatterers. Their dimensions range from 100 nm to 6 μm, and thus fall within the NIR window. Most of these organelles fall in the Mie region, and exhibit highly anisotropic forward-directed scattering.

As the above only gives a scattering coefficient anisotropic factor for the entire retina, and not for the RPE layer that forms the back layer of the retina individually, the RPE scattering coefficient and an anisotropic factor is approximated by using the total retinal quantities. As the scattering coefficient is only given at a single wavelength and since the scattering has been determined as being primarily in the Mie region, We shall apply the $\lambda^2$ factor of eq. [5.9] to determine the scattering coefficients at other wavelengths:

$$\mu_{backscatRET} = (1-0.97)120(\lambda_{nm}/855)^2 = 4.92 \times 10^{-6} \lambda_{nm}^2 \text{ cm}^{-1} \quad [10a]$$

$$\mu_{backscatCH} = (1-0.97)275(\lambda_{nm}/855)^2 = 3.76 \times 10^{-5} \lambda_{nm}^2 \text{ cm}^{-1} \quad [10b]$$

These can be compared with the scattering coefficients from melanin for normal melanosome densities ($N_{RPE}$=2×10$^{10}$ cm$^{-3}$ and $N_{CH}$=5.4×10$^9$ cm$^{-3}$)

$$\mu_{sRPE} = 2 \times 10^{10} \times 0.05 \times 10^{-14} \lambda_{nm}^2 = 1 \times 10^{-5} \lambda_{nm}^2 \text{ cm}^{-1}$$
[normal RPE melanin density] [11a]

$$\mu_{sCH} = 5.4 \times 10^9 \times 0.03 \times 10^{-14} \lambda_{nm}^2 = 1.62 \times 10^{-6} \lambda_{nm}^2 \text{ cm}^{-1}$$
[normal choroid melanin density] [11b]

We see that scattering from the structural matrix in the RPE is less than that from the melanin, whereas in the choroid the scattering from the structural matrix is larger by an order of magnitude.

The scattering coefficients are smaller than the coefficients of absorption at normal melanin densities $$\mu_{aRPE} = 2 \times 10^{10} \times 9.47 \times 10^{-7} \exp[-0.0062 \lambda_{nm}] = 10.89 \times 10^4 \exp[-0.0062 \lambda_{nm}] \quad [12a]$$

$$\mu_{aCH} = 5.4 \times 10^9 \times 9.47 \times 10^{-7} \exp[-0.0062 \lambda_{nm}] = 5.11 \times 10^3 \exp[-0.0062 \lambda_{nm}] \quad [12a]$$

The melanosome number densities and scattering cross sections indicate that not much scattering occurs in traversing either the RPE or the choroid for radiation with wavelengths in the 600-800 nm range of wavelengths. For the 200 micron thick choroid, the typical melanosome density is 5.4×10$^9$ cm$^{-3}$, and with a back scattering coefficient equal to the sum of eqs. [10b] and [11b], this gives an effective mean free path for scattering of an 800 nm photon:

$$\Lambda_{mfp} = 1/25 = 0.04 \text{ cm, i.e. 400 microns.} \quad [12]$$

This is larger than the thickness of the choroid. The optical density for scattering in the choroid is:

$$OD_{scattering \text{ in } choroid} = \mu_{scat} L_{CH} = (200/400)(1/2.303) = 0.22 \quad [13]$$

This is much less than the optical density for absorption by the melanin. The scattering optical density in the anterior retina is also small.

In the RPE with a melanosome density of 2×10$^{10}$ cm$^{-3}$, the mean free path given by eqs. [10a] and [11a] is:

$$\Lambda_{mfp} = 1/9.54 = 0.0.1 \text{ cm, i.e. 1000 microns.} \quad [14]$$

This is much larger than the 6-10 micron thickness of the RPE, so the probability that a photon is scattered on traversing the RPE is very small indeed. The optical density for scattering in the RPE is:

$$OD_{scattering\ in\ RPE} = \mu_{scat} w = 9.54 \times 0.0006/2.303 = 0.004. \quad [15]$$

As in the choroid, this is quite a bit less than the optical density for absorption by the melanin.

Accordingly, in the 600-800 nm range of wavelengths, absorption is more important than scattering both in the RPE and choroid. This then leads to the simple photon transport equations.

We use the simple Kubelka-Munk equations here in order to develop a simple intuition for the dependence of the reflectometry results on the relevant parameters.

Consider first the RPE. The approximate transport equations in the steady state are:

$$dI(+)/dx = -[N(\sigma_s + \sigma_a) + \mu_{back\ scat}]I(+) + [N\sigma_s + \mu_{back\ scat}]I(-) \quad [16]$$

$$dI(-)/dy = -[N(\sigma_s + \sigma_a) + \mu_{back\ scat}]I(-) + [N\sigma_s + \mu_{back\ scat}]I(-) \quad [17]$$

Here, $I(+)$ is the intensity of the input radiation as it travels through the RPE $I(-)$ is the intensity of the reflected radiation as it travels backwards through the RPE to the front of the RPE.

x is the distance into the RPE measured from the front of the RPE y=w−x, where w is the thickness of the RPE melanin layer N is the number density of the melanin aggregates that absorb and scatter the radiation $\sigma_s$ denotes the cross section of a melanin aggregate for backwards scattering $\sigma_a$ denotes the cross section of a melanin aggregate for absorption $\mu_{back\ scat}$ is the coefficient for backscattering for the structural matrix It has previously been demonstrated experimentally that $\sigma_s/(\sigma_s+\sigma_a)$ is quite large, scattering contributing less than 6% to the total optical attenuation across all wavelengths in the UV and optical range.

The quantity $N(\sigma_s+\sigma_a)$ w is simply 2.303× the total attenuation (absorption plus scattering) optical density of the RPE melanin layer.

Equations [16] and [17] can be further simplified by ignoring the term $+N\sigma_s I(-)$ in eq. [16], the rationale for this being that the reflected signal I(−) is much smaller than the input signal I(+). Then, on requiring that:

$I(+)$ at $x=0$ equals the input intensity $I_o$ [18a]

$I(-)$ at $x=w$ equals $R_{CH} I(+)$ at $x=w$ [18b]

where:

$R_{CH}$ is the reflection coefficient at the interface between the ROE and choroid.

The 10 micron thick blood-rich choriocapillaris does not contain any melanin, and can be ignored in the 600 nm-750 nm range of wavelengths.

The equations can be solved directly to give for the reflection coefficient $R_{RPE}$ at x=0

$$R_{RPE} = I(-) \text{ at } x=0/I_o$$

$$= \{N\sigma_s + \mu_{backscat}\}_{RPE} / \{2N(\sigma_s+\sigma_a) + \mu_{backscat}\}_{RPE}$$

$$+ \exp[-2w\{N(\sigma_s+\sigma_a) + \mu_{backscat}\}_{RPE}][R_{CH} - \{N\sigma_s + \mu_{backscat}\}_{RPE}/\{2N(\sigma_s+\sigma_a) + \mu_{backscat}\}_{RPE}] \quad [19]$$

The subscript "RPE" has been added in eq. [19] to indicate that the quantities are for the RPE.

In the same manner, an expression for the reflection coefficient $R_{CH}$ at the RPE/choroid interface can be obtained:

$$R_{CH} = \{N\sigma_s + \mu_{backscat}\}_{CH} / \{2N(\sigma_s+\sigma_a) + \mu_{backscat}\}_{CH}$$

$$+ \exp[-2d_{CH}\{N(\sigma_s+\sigma_a) + \mu_{backscat}\}_{CH}][R_{SC} - \{N\sigma_s + \mu_{backscat}\}_{CH}/\{2N(\sigma_s+\sigma_a) + \mu_{backscat}\}_{CH}] \quad [20]$$

Finally, the total reflection coefficient (at the front of the retina) is given by the same equations to be:

$$R_{TOT} = 1 - (1 - R_{RPE}) \exp[-2\mu_{back\ scatRET} d_{RET}] \quad [21]$$

where $\mu_{back\ scatRET}$ is the backwards scattering coefficient of the retinal structural matrix.

In these expressions, the subscript "CH" has been added to denote that the corresponding quantities are to be evaluated for choroid $d_{CH}$ denotes the thickness of the choroid (200 microns)

$d_{RET}$ is the thickness of the anterior retina (200 microns)

$R_{SC} = 0.5\exp[-0.00261(\lambda_{nm}-675)]$ denotes the reflection coefficient at the sclera at the back of the choroid.

Insertion of eqs. {19] and [20] into eq. [21] results in the desired overall reflection coefficient.

In the reflectivity, cross-sections for the melanosomes in the RPE and for the melanosomes for the choroid both appear. As indicated above, these melanosomes are quite different. The melanin in the RPE is derived from the neural ectoderm, whereas the choroidal melanin is derived from the neural crest. Melanosomes in the RPE have been found to be different from those in the choroid. In the RPE, the melanosomes are located mainly in the apical region of the RPE cells and are quite elongated in shape, with the long dimension aligned with the apices in order to make close contact with the rods and cones. A typical width for an RPE melanosome has been found to be approximately 300 nm, whereas the typical length is 720 nm. In the choroid, the melanosomes do not need to be elongated and are primarily globular in shape. The differences in the shapes lead to the differences in the cross-sections as noted above. The melanin sheets stack to form the aggregates in a melanosome, and thus the RPE melanosomes are represented as lossy dielectric prolate spheroids. The globular melanosomes of the choroid are represented by lossy spherical dielectrics.

With respect to numerical results for the eye, the wavelength-dependent quantities in the reflection coefficient are summarized below:

From the Structural Matrix:

$$\mu_{backscatRET} = 4.92 \times 10^{-6} \lambda_{nm}^2 \text{ cm}^{-1} \quad [22a]$$

$$\mu_{backscatRPE} = 4.92 \times 10^{-6} \lambda_{nm}^2 \text{ cm}^{-1} \quad [22b]$$

$$\mu_{backscatCH} = 3.76 \times 10^{-5} \lambda_{nm}^2 \text{ cm}^{-1} \quad [23]$$

Melanin Related:

$$\sigma_{sRPE} = 0.03 \times 10^{-14} \lambda_{nm}^2 \text{ cm}^2 \quad [24]$$

$$\sigma_{sCH} = 0.05 \times 10^{-10} \lambda_{nm}^2 \text{ cm}^2 \quad [25]$$

$$\sigma_a = 9.47 \times 10^{-7} \exp[-0.0062 \lambda_{nm}] \text{ cm}^2 \quad [26]$$

$$N_{RPE} = 2 \times 10^{10} \text{ cm}^{-3} \text{ for a normal patient} \quad [27a]$$

$$N_{CH} = 5.4 \times 10^9 \text{ cm}^{-3} \text{ for a normal patient} \quad [27b]$$

Relevant Dimensions:

$$w=0.0006 \text{ cm} \quad [28a]$$

$$d_{CH}=0.0200 \text{ cm} \quad [28b]$$

It is interesting that eq. [23] for the reflectivity depends on only the five parameter combinations:

$$\{\sigma_s/2(\sigma_s+\sigma_a)\}_{CH}$$

$$\{\sigma_s/2(\sigma_s+\sigma_a)\}_{RPE}$$

$$\exp[-2\mu_{backscatRET}d_{RET}]$$

$$\exp[-2(\{N(\sigma_s+\sigma_a)\}_{RPE}+\mu_{backscatRPE})w]$$

$$\exp[-2\{N(\sigma_s+\sigma_a)\}_{CH}+\mu_{backscatCH})d_{CH}]$$

The fourth (exponential) parameter combination provides the desired sensitive measure of the RPE melanin concentration $N_{RPE}$.

FIGS. 8-15 are graphs providing the implications of equations [19]-[21], and particularly equation [21] for the overall reflectivity of the anterior retina, RPE and choroid. They display variations in the parameters with wavelengths, RPE and choroid melanosome number densities.

Figure 8:
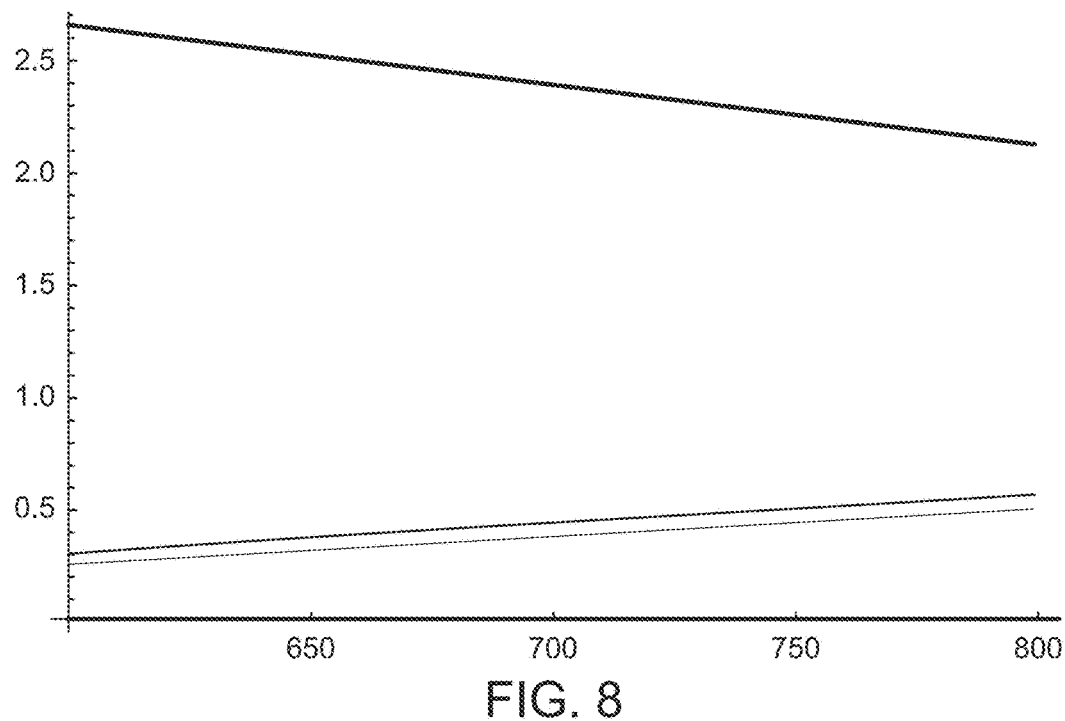
FIG. 8 is a graph depicting a comparison of RPE melanin absorption coefficient, melanin scattering coefficient, and structural matrix scattering coefficient.

With reference to FIG. 8, a comparison of RPE melanin absorption coefficient (top curve), RPE melanin scattering coefficient (middle curve) and RPE structural matrix scattering coefficient (bottom curve) is shown. The logs (to the base 10) of the coefficients are shown, with the coefficients expressed in $cm^{-1}$. The logarithms are plotted versus wavelengths and nanometers between 600 nm and 800 nm. A normal RPE melanosome concentration of $2 \times 10^{10}$ cm$^{-3}$ has been assumed. FIG. 8 shows that in the RPE at normal melanosome densities, the absorption coefficient is largest followed by the scattering coefficient due to the melanin and the scattering coefficient of the structural matrix. A drastic reduction in the melanosome density would have to occur before the scattering coefficients become as large as the absorption coefficient.

Figure 9:
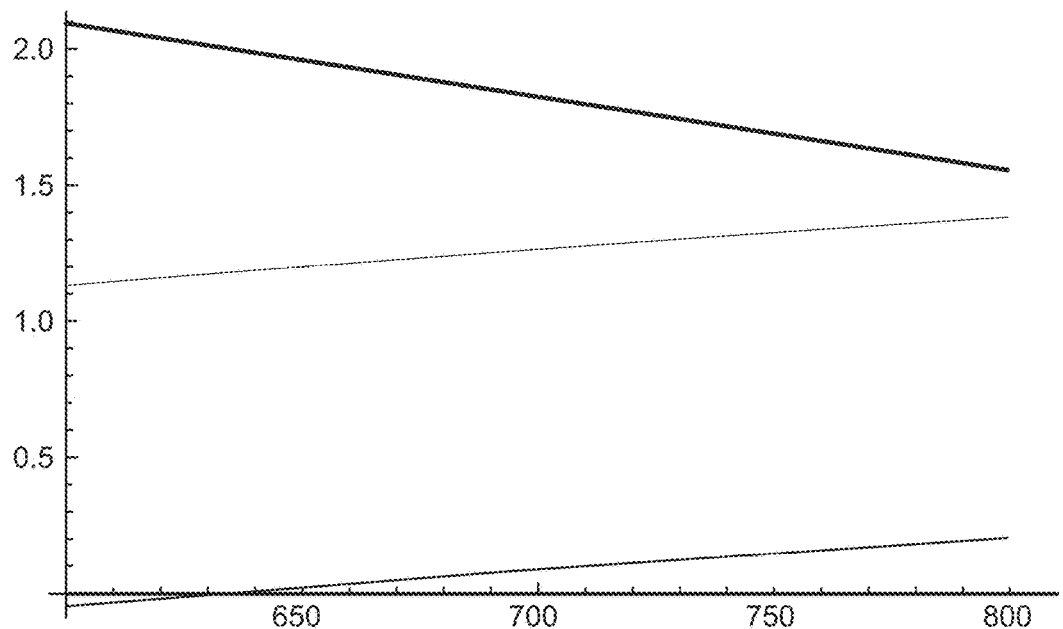
FIG. 9 is a graph depicting a comparison of choroid melanin absorption coefficient, choroid melanin scattering coefficient, and choroid structural matrix scattering coefficient.

With reference now to FIG. 9, a comparison of choroid melanin absorption coefficient (top curve), choroid melanin scattering coefficient (bottom curve), and choroid structural matrix scattering coefficient (middle curve) is shown. The logs (to the base 10) of the coefficients are shown, with the coefficients expressed in $cm^{-1}$. The logarithms are plotted vs wavelengths in nanometers between 600 nm and 800 nm. A normal choroid melanosome concentration of $5.4 \times 10^9$ cm$^{-3}$ has been assumed in these plots. In the choroid at normal melanosome densities, the absorption coefficient due to the melanosomes is the largest, followed by the scattering coefficient from the structural matrix, with a much smaller scattering coefficient from the melanosomes. However, the difference between the melanosome absorption coefficient and the matrix scattering coefficient is small at 800 nm. If the choroid melanosome density decreases, the matrix scattering coefficient can become larger than the melanosome absorption coefficient. This is especially true at wavelengths near 800 nm.

As seen from eqs. [19]-[21], the total reflectivity is determined by the reflectivities of the RPE and of the choroid, i.e. by $R_{RPE}$ and $R_{CH}$. These are shown in FIGS. 10 and 11.

Figure 10:
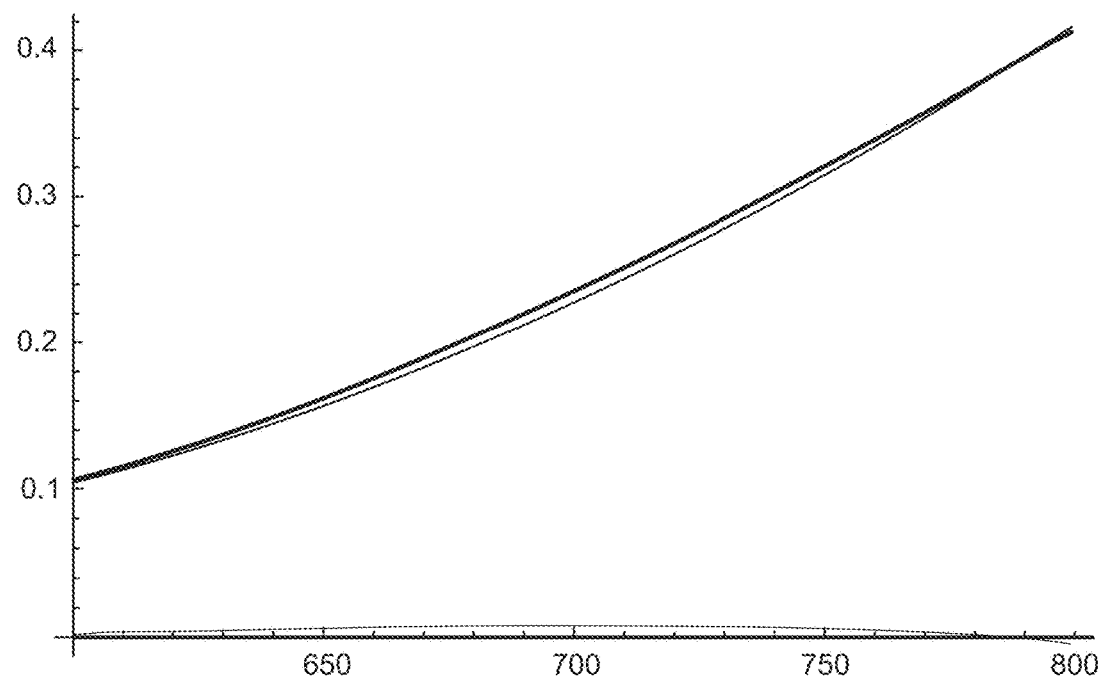
FIG. 10 is a graph depicting the reflectivity of choroid as a function of wavelength at a normal choroid melanosome density.

FIG. 10 is a graph illustrating reflectivity $R_{CH}$ of choroid (top curve) as a function of wavelength (in nm), at a normal choroid melanosome density ($5.4 \times 10^9$ cm$^{-3}$). Two other curves are also shown, one for each of the components of eq. [20] comprising the expression for $R_{CH}$. The middle curve is the fractional term containing the choroid scattering coefficients in the numerator and the sum the of the scattering and absorption coefficients in the denominator. The bottom curve is the exponential term with its factor. FIG. 10 shows that the reflectivity increases as the wavelength increases. This results from the increase in the (backwards) scattering coefficient with wavelength in the Mie regime of scattering. By far the dominant contribution to the reflectivity of the choroid at normal choroid melanosome densities is the fraction containing the ratios of the scattering and absorption coefficients. The exponential term is quite negligible.

Figure 11:
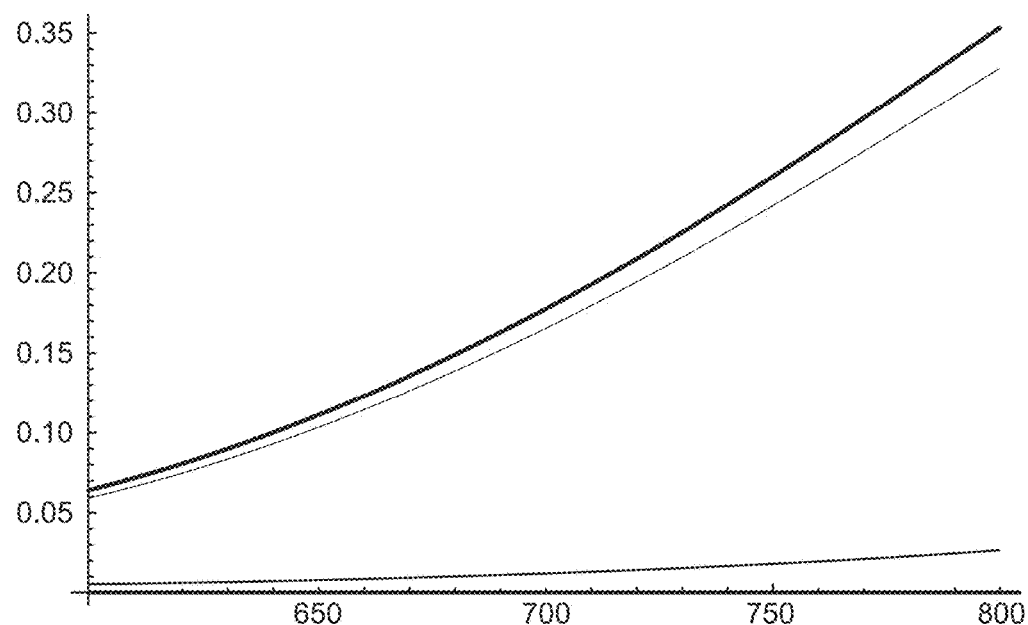
FIG. 11 is a graph depicting the reflectivity of RPE as a function of wavelength at normal RPE and choroid melanosome densities.

FIG. 11 is a graph depicting reflectivity $R_{RPE}$ of RPE (top curve) as a function of wavelength (in nm), at normal RPE and choroid melanosome densities ($2 \times 10^{10}$ cm$^{-3}$ and $5.4 \times 10^9$ cm$^{-3}$, respectively). Two other curves are also shown, one for each of the components of eq. [19] comprising the expression for $R_{RPE}$. The middle curve is the fractional term containing the RPE scattering coefficients in the numerator and the sum the of the scattering and absorption coefficients in the denominator. The bottom curve is the exponential term with its factor that contains $R_{CH}$. FIG. 11 shows that the reflectivity increases as the wavelength increases, just as with the reflectivity from the choroid. Again, this results from the increase in the (backwards) scattering coefficient with wavelength in the Mie regime of scattering. By far the dominant contribution to the reflectivity of the RPE at normal RPE and choroid melanosome densities is the fraction containing the ratios of the RPE scattering and absorption coefficients. The exponential term is much smaller, due to the large RPE absorption coefficient due to the melanosomes.

Figure 12:
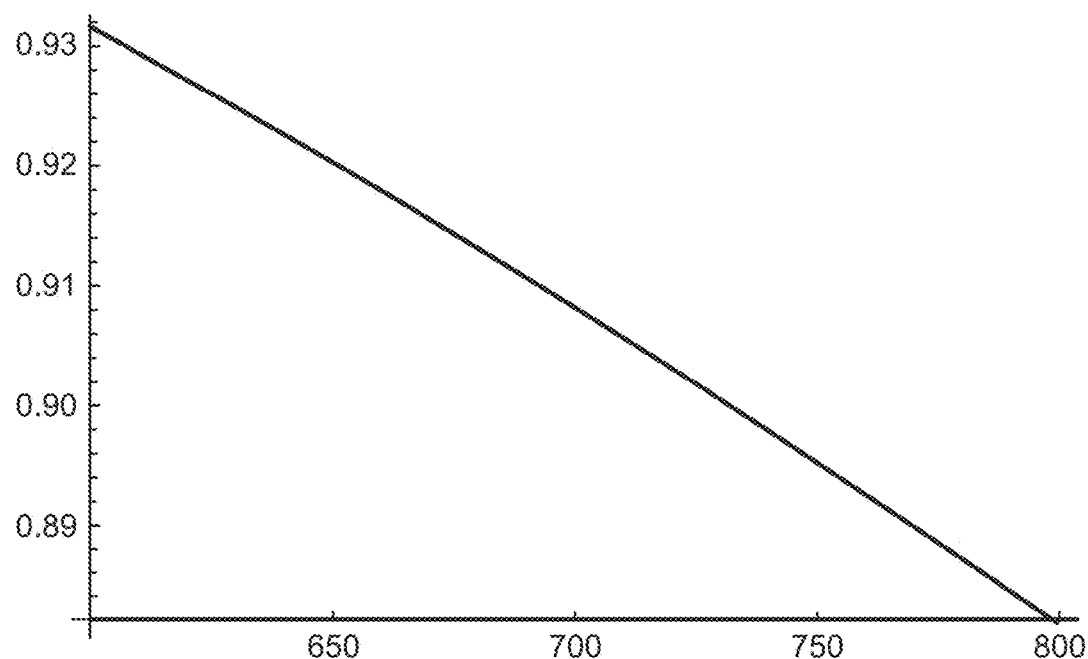
FIG. 12 is a graph depicting a transmission factor of anterior retina versus wavelength.

FIG. 12 illustrates that equation [21] shows how the total reflectivity $R_{TOT}$ is derived from the reflectivity of the RPE $R_{RPE}$, contains an exponential attenuation factor that contains the extinction coefficient due to scattering in the anterior retina. FIG. 12 illustrates the transmission factor of the anterior retina as given by the exponential factor of equation [21] versus the wavelength in nanometers. The transmission of the reflected radiation through the anterior retina is quite good, varying from 93+% at 600 nm to 88+% at 800 nm.

It should be noted that the RPE melanin concentration varies with lateral position in the eye. It peaks at the center of the macula and then decreases on either side over a range of approximately 5° to a relatively constant value for about 10° on either side, before rising again towards the equator at −20° and +15°. To get consistent results, it is best to operate the detector 110, preferably a reflectometer in accordance with the present invention, in the regions where the concentration is relatively constant, or in other words on the order of approximately 10° away from the center of the macula.

The foregoing figures, including FIGS. 5-12, show the behavior at normal RPE and normal choroid melanosome densities ($2 \times 10^{10}$ cm$^{-3}$ and $5.4 \times 10^9$ cm$^{-3}$ respectively. The present invention is particularly interested in how the total reflectivity $R_{TOT}$ changes as the RPE melanosomes densities change. This is illustrated and described in connection with FIGS. 13-15.

Figure 13:
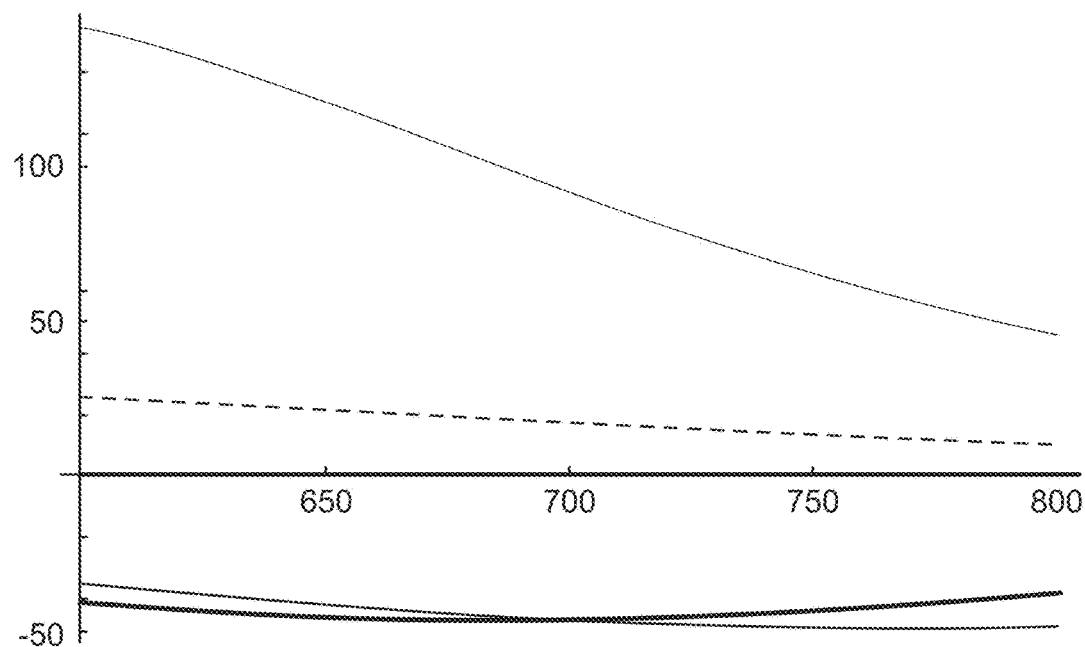
FIG. 13 is a graph depicting percentage changes in total reflectivity as a function of wavelength as RPE and choroid melanosome densities vary from the normal.

FIG. 13 illustrates the percentage changes in the total reflectivity $R_{TOT}$ as a function of wavelength in nanometers, as RPE and choroid melanosome densities vary from the normal $n_{RPE}=2 \times 10^{10}$ cm$^{-3}$ and $n_{CH}=5.4 \times 10^9$ cm$^{-3}$. Four curves are shown. The top curve is for a normal RPE density and a choroid density that is ⅙ normal ($n_{RPE}$ and (⅙) $n_{CH}$). The upper middle curve is for (⅙) $n_{RPE}$ and $n_{CH}$. The lower middle curve is for $n_{RPE}$ and $6n_{CH}$. The lowest curve (at 600 nm) is for $6n_{RPE}$ and $n_{CH}$. FIG. 13 shows that comparable percentage changes occur in $R_{TOT}$ from comparable changes in RPE melanosome densities and in choroid melanosome densities, but that the changes from RPE densities have a different wavelength dependence from changes in choroid densities. Accordingly, measurements of the percentage changes in the total reflectivity at two different wavelengths can uniquely determine what the changes in RPE and choroid melanosome densities are.

Figure 14:
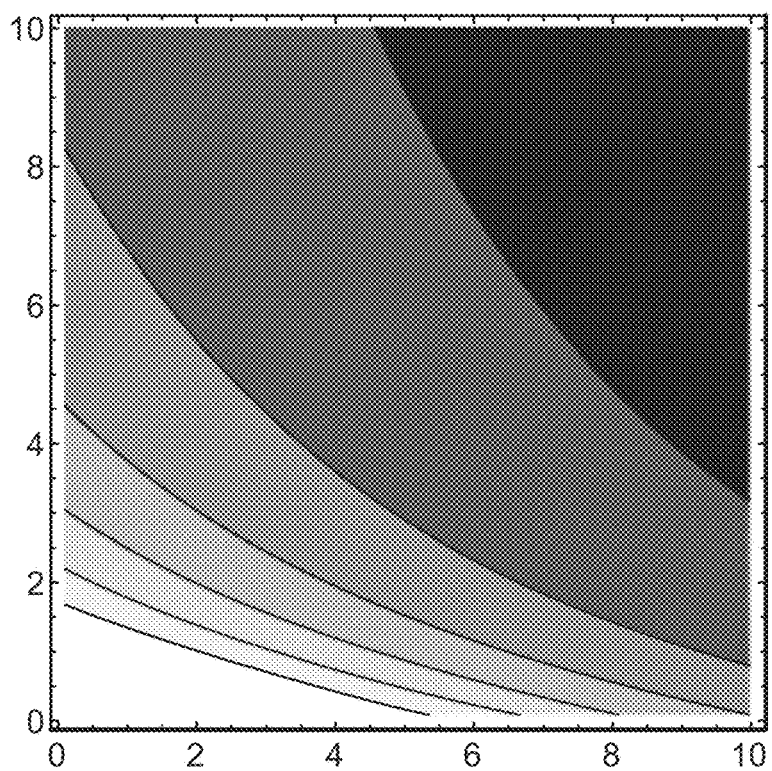
FIG. 14 is a contour plot at a first wavelength of percentage change in the total reflectivity in accordance with two-wavelength reflectometry, in accordance with the present invention.
Figure 15:
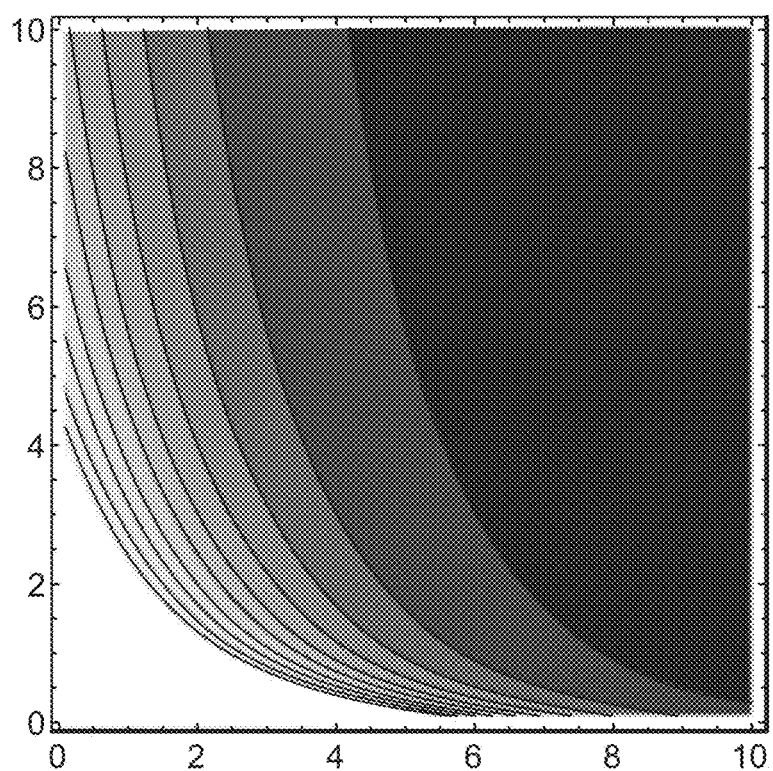
FIG. 15 is a contour plot at a second wavelength of the percentage change in the total reflectivity in accordance with two-wavelength reflectometry, in accordance with the present invention.

The use of dual-wavelength reflectometry to determine both the RPE melanosomes density or concentration and the choroid melanosome density or concentration is further illustrated in FIGS. 14 and 15. FIGS. 14 and 15 are contour plots of percentage change in the total reflectivity as a function of $r=n_{RPE}(\text{abnormal})/n_{RPE}(\text{normal})$ on the abscissa (x-axis) and $c=n_{CH}(\text{abnormal})/n_{CH}(\text{normal})$ on the ordinate (y-axis). FIG. 14 shows the plot at 600 nm, and FIG. 15 shows the plot at 800 nm. It is apparent that the percentage change contours at 600 nm have a different shape than the contours at 800 nm. A given percentage change at 600 nm and another given percentage change at 800 nm then provide two different contours, and the intersection of these two contours provides uniquely the abnormal melanosome densities for both the RPE and the choroid. One way to solve the expressions for the unique RPE and choroid melanosome densities that give the measured reflectivities at the two wavelengths may be simply to store in computer memory a look-up table of the reflectivity contours at two different wavelengths in the 600-800 nm range of wavelengths, and to look for the two contours corresponding to the measurements to find the one common pair of RPE and choroid densities. Alternatively, the pertinent equations above can be solved, such as using a computer or other electronic device.

The curves in the figures herein have been generated with approximate expressions, so the absolute magnitudes of the reflection coefficient shown (of the order of a few percent) should be taken as estimates of the actual reflection coefficient. The actual value will depend upon the specifics of the detectors optics and geometry. A baseline may be established from a population of normal patients, from which deviations can be established. Thus, FIGS. 14 and 15 show percentage change contours for abnormalities rather than absolute value contours of the reflectivity.

Although several embodiments have been described in detail for purposes of illustration, various modifications may be made without departing from the scope and spirit of the invention. Accordingly, the invention is not to be limited, except as by the appended claims.

What is claimed is:

1. A process for providing safe treatment of an eye based on a determination of a concentration of melanin within a retinal pigment epithelium of the eye, comprising the steps of:
    generating a first light beam having a wavelength between 550 nm and 900 nm;
    applying the first light beam to a retinal pigment epithelium and a choroid of the eye;
    generating a second light beam having a wavelength between 550 nm and 900 nm that is of a different wavelength than the first light beam;
    applying the second light beam to the retinal pigment epithelium and the choroid of the eye;
    using a detector device to measure the amount of light reflected from the retinal pigment epithelium and the choroid by the first and second light beams;
    determining a concentration of melanin within the retinal pigment epithelium and the choroid of the eye using the measured amount of light reflected from the retinal pigment epithelium and the choroid of the eye from the first and second light beams; and
    adjusting parameters of a treatment of the eye if the determined concentration of melanin within the retinal pigment epithelium of the eye exceeds a predetermined amount.

2. The process of claim 1, wherein the measuring step comprises using a reflectometer to measure the amount of light reflected from the retinal pigment epithelium and the choroid of the eye from the first and second light beams.

3. The process of claim 1, wherein the first and second light beams differ in wavelength by at least 25 nm.

4. The process of claim 1, wherein the first and second light beams each have a wavelength between 600 nm and 850 nm.

5. The process of claim 1, including the step of distinguishing the amount of light reflected by the first and second light beams from the retinal pigment epithelium and the choroid.

6. The process of claim 1, including the step of adjusting parameters of a photocoagulation or a photostimulation treatment of the eye to avoid overheating the retina.

7. The process of claim 6, including the step of lowering the power of a light beam applied to the eye during photocoagulation or photostimulation treatment of the eye.

8. The process of claim 1, wherein the determining step comprises the step of calculating a total reflection coefficient according to an approximate expression of:

$$R_{TOT}=1-(1-R_{RPE})\exp[-2\mu_{back\ scatRET}d_{RET}];$$

wherein $\mu_{back\ scatRET}$ is the backwards scattering coefficient of the retinal structural matrix;
wherein $d_{RET}$ is the thickness of the anterior retina; and
wherein $R_{RPE}$ is the reflection coefficient for the retina.

9. The process of claim 8, wherein the reflection coefficient for the retina is calculated according to an approximate expression of:

$$R_{RPE}=I(-) \text{ at } x=0/I_o;$$

$$=\{N\sigma_s+\mu_{backscat}\}_{RPE}/\{2N(\sigma_s+\sigma_a)+\mu_{backscat}\}_{RPE};$$

$$+\exp[-2w\{N(\sigma_s+\sigma_a)+\mu_{backscat}\}_{RPE}][R_{CH}-\{N\sigma_s+\mu_{backscat}\}_{RPE}/\{2N(\sigma_s+\sigma_a)+\mu_{backscat}\}_{RPE}];$$

wherein $R_{RPE}$ is the reflection coefficient for the retinal pigment epithelium;
wherein $I(-)$ is the intensity of the reflected radiation as it travels backwards through the RPE to the front of the RPE;
wherein $I_0$ is the input intensity;
wherein $\sigma_s$ denotes the cross-section of a melanin aggregate for backwards scattering;
wherein $\sigma_a$ denotes the cross-section of a melanin aggregate for absorption;
wherein $\mu_{backscat}$ is the coefficient for backscattering for the structural matrix;
wherein N is the number density of the melanin aggregates that absorb and scatter the radiation; and
wherein $R_{CH}$ is the reflection coefficient at the interface between the RPE and choroid.

10. The process of claim 9, wherein the calculating the total reflection coefficient comprises calculating the reflection coefficient at the retinal pigment epithelium and choroid interface, according to an approximate expression of:

$$R_{CH} = \{N\sigma_s + \mu_{backscat}\}_{CH}/\{2N(\sigma_s+\sigma_a)+\mu_{backscat}\}_{CH};$$

$$+\exp[-2d_{CH}\{N(\sigma_s+\sigma_a)+\mu_{backscat}\}_{CH}][R_{SC}-\{N\sigma_s+\mu_{backscat}\}_{CH}/\{2N(\sigma_s+\sigma_a)+\mu_{backscat}\}_{CH}];$$

wherein N is the number density of the melanin aggregates that absorb and scatter the radiation; and wherein $d_{CH}$ denotes the thickness of the choroid.

11. A process for providing safe treatment of an eye based on a determination of a concentrations of melanin within a retinal pigment epithelium of the eye, comprising the steps of:
- generating a first light beam and a second light beam each having a wavelength between 600 nm and 850 nm, wherein the first and second light beams have a different wavelength;
- applying the first and second light beams to a retinal pigment epithelium and a choroid of the eye;
- using a reflectometer to measure the amount of light reflected from the retinal pigment epithelium and the choroid by the first and second light beams;
- determining a concentration of melanin within the retinal pigment epithelium and the choroid of the eye using the measured amount of light reflected from the retinal pigment epithelium and the choroid of the eye from the first and second light beams; and
- adjusting parameters of a treatment of the eye if the determined concentration of melanin within the retinal pigment epithelium of the eye exceeds a predetermined amount.

12. The process of claim 11, including the step of distinguishing the amount of light reflected by the first and second light beams from the retinal pigment epithelium and the choroid.

13. The process of claim 11, wherein the first and second light beams differ in wavelength by at least 25 nm.

14. The process of claim 11, wherein the adjusting step comprises adjusting parameters of a photocoagulation or a photostimulation treatment of the eye to avoid overheating the retina if the determined concentration of melanin within the retinal pigment epithelium of the eye is above the predetermined amount.

15. The process of claim 14, wherein the adjusting parameters step includes the step of lowering the power of a light beam applied to the eye during photocoagulation or photostimulation treatment of the eye.

16. The process of claim 11, wherein the determining step comprises the step of calculating a total reflection coefficient according to an approximate expression of:

$$R_{TOT} = 1-(1-R_{RPE})\exp[-2\mu_{back\ scatRET}d_{RET}];$$

wherein $\mu_{back\ scatRET}$ is the backwards scattering coefficient of the retinal structural matrix;

wherein $d_{RET}$ is the thickness of the anterior retina; and wherein $R_{RPE}$ is the reflection coefficient for the retina.

17. The process of claim 16, wherein the reflection coefficient for the retina is calculated according to an approximate expression of:

$$R_{RPE} = I(-) \text{ at } x=0/I_o;$$

$$= \{N\sigma_s+\mu_{backscat}\}_{RPE}/\{2N(\sigma_s+\sigma_a)+\mu_{backscat}\}_{RPE};$$

$$+\exp[-2w\{N(\sigma_s+\sigma_a)+\mu_{backscat}\}_{RPE}][R_{CH}-\{N\sigma_s+\mu_{backscat}\}_{RPE}/\{2N(\sigma_s+\sigma_a)+\mu_{backscat}\}_{RPE}];$$

wherein $R_{RPE}$ is the reflection coefficient for the retinal pigment epithelium;

wherein $I(-)$ is the intensity of the reflected radiation as it travels backwards through the RPE to the front of the RPE;

wherein $I_0$ is the input intensity;

wherein $\sigma_s$ denotes the cross-section of a melanin aggregate for backwards scattering;

wherein $\sigma_a$ denotes the cross-section of a melanin aggregate for absorption;

wherein $\mu_{backscat}$ is the coefficient for backscattering for the structural matrix;

wherein N is the number density of the melanin aggregates that absorb and scatter the radiation; and wherein $R_{CH}$ is the reflection coefficient at the interface between the RPE and choroid.

18. The process of claim 17, wherein the calculating the total reflection coefficient comprising calculating the reflection coefficient at the retinal pigment epithelium and choroid interface, according to an approximate expression of:

$$R_{CH} = \{N\sigma_s+\mu_{backscat}\}_{CH}/\{2N(\sigma_s+\sigma_a)+\mu_{backscat}\}_{CH};$$

$$+\exp[-2d_{CH}\{N(\sigma_s+\sigma_a)+\mu_{backscat}\}_{CH}][R_{SC}-\{N\sigma_s+\mu_{backscat}\}_{CH}/\{2N(\sigma_s+\sigma_a)+\mu_{backscat}\}_{CH}];$$

wherein N is the number density of the melanin aggregates that absorb and scatter the radiation; and wherein dcH denotes the thickness of the choroid.

* * * * *